United States Patent [19]

Venkatasetty

[11] Patent Number: 4,521,290
[45] Date of Patent: Jun. 4, 1985

[54] THIN LAYER ELECTROCHEMICAL CELL FOR RAPID DETECTION OF TOXIC CHEMICALS

[75] Inventor: Hanumanthiya V. Venkatasetty, Burnsville, Minn.

[73] Assignee: Honeywell Inc., Minneapolis, Minn.

[21] Appl. No.: 590,309

[22] Filed: Mar. 16, 1984

[51] Int. Cl.³ ............................................ G01N 27/54
[52] U.S. Cl. ..................................... 204/412; 204/415
[58] Field of Search ............... 204/412, 415, 411, 431, 204/432

[56] References Cited

U.S. PATENT DOCUMENTS

| | | | |
|---|---|---|---|
| 3,260,656 | 7/1966 | Ross ................................. | 204/412 X |
| 4,169,779 | 10/1979 | Tataria et al. ........................ | 204/412 |
| 4,184,937 | 1/1980 | Tataria et al. ........................ | 204/412 |
| 4,267,023 | 5/1981 | Frant et al. ......................... | 204/1 T |
| 4,324,257 | 4/1982 | Albarda et al. ..................... | 128/635 |

FOREIGN PATENT DOCUMENTS 2627271  12/1977  Fed. Rep. of Germany ...... 204/412

Primary Examiner—G. L. Kaplan
Attorney, Agent, or Firm—Omund R. Dahle

[57] ABSTRACT

A thin-layer electrochemical cell for rapid detection of toxic chemicals and chemical agents having a large area thin-film sensing electrode in contact with a very thin layer of nonaqueous aprotic organic based electrolyte solution, and having the reference electrode on the same plane and the counter electrode positioned in a different plane beyond the edge of the large area sensing electrode.

22 Claims, 3 Drawing Figures

THIN LAYER ELECTROCHEMICAL CELL FOR RAPID DETECTION OF TOXIC CHEMICALS

BACKGROUND AND SUMMARY OF THE INVENTION

The invention is directed to the field of badge type electrochemical gas trace sensors and particularly one using a thin layer electrochemical cell with large area thin film sensing electrode formed on a porous membrane in contact with a very thin layer of nonaqueous aprotic organic based electrolyte solution.

The present invention is related to a copending application of the present applicant, Ser. No. 557,037 (now abandoned) entitled "An Electrochemical Sensor for Multiagent Detection on Aprotic Organic Electrolyte Solution," assigned to the same assignee as the present invention, filed Dec. 1, 1983, and to a copending application Ser. No. 570,152 (now abandoned) of H. V. Venkatasetty and J. D. Zook, entitled "Electrochemical Passive Chemical Agent Detector," assigned to the same assignee as the present invention, and filed Jan. 12, 1984, the teachings of both of which are incorporated herein by reference.

Electrochemical gas sensors require a structure to contain the electrolyte. It is important that the structure be efficient in transferring the molecules to be sensed to the working electrode without being trapped at surfaces where they are precluded from reaching the working electrode. In the second copending application cited above a badge type electrochemical sensor with a nonaqueous electrolyte solution is designed as a small thin sandwich cell configuration which employs a working electrode of platinum film on a gas and vapor molecule permeable polymer membrane, with two counter electrodes of platinum film and a suitable reference electrode such as $Ag/Ag^+$.

The present invention is particularly directed to a thin-layer electrochemical cell with a large area thin film sensing electrode in contact with a very thin layer of electrolyte ($\sim 10^{-2}$ mm) with counter and reference electrodes suitably placed. Electrochemical oxidation or reduction of the electroactive chemical, toxic chemical or chemical agent can be quantitatively completed in less than two seconds. Using nonaqueous aprotic organic based electrolyte solutions with wide voltage window in which chemical agents are more soluble, the cell can be used for multiagent detection with improved sensitivity.

DESCRIPTION

Figure 1:
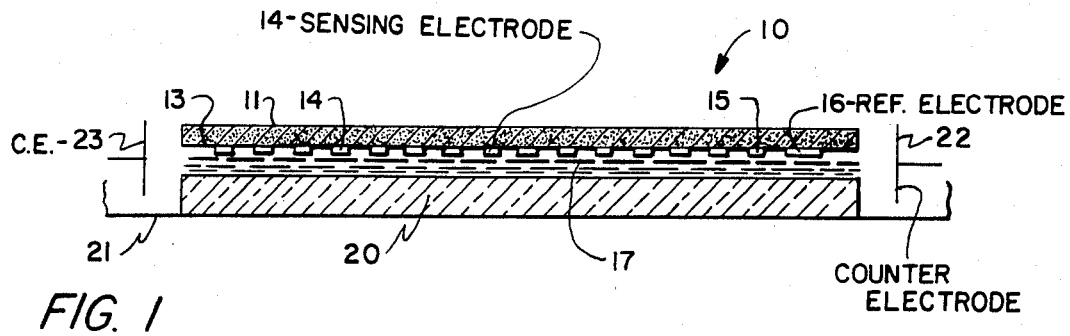
FIG. 1 is a cross section of the fabrication of the electrochemical cell according to the invention.
Figure 2:
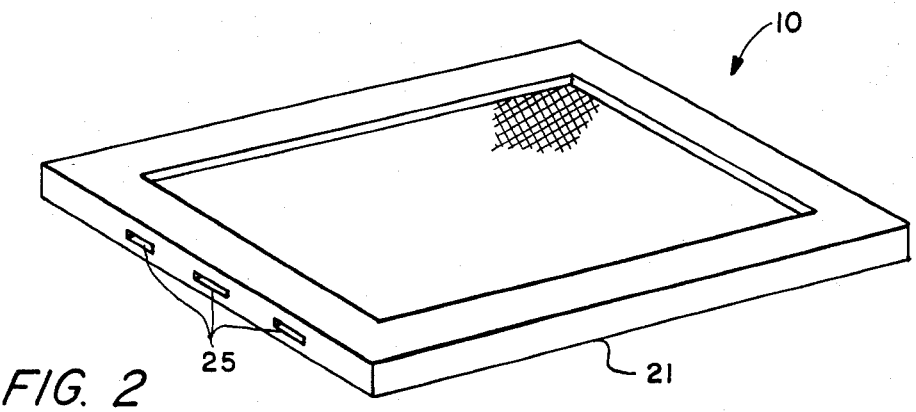
FIG. 2 is a pictorial representation of the badge type sensor.

A badge type thin film electrochemical gas trace sensor 10 according to the invention is shown pictorially in FIG. 2 and in cross section in FIG. 1. The thickness of the thin film structure as shown in FIG. 1 is exaggerated for illustrative purposes in the drawings. At the surface of the sensor cell a porous polymer membrane 11, such as polytetrafluoroethylene (PTFE), is fabricated. The porous membrane preferably has many parallel cylindrical pores. The fabricated pore size is a few microns resulting in a great many pores in the cell area of about 5 square centimeters. The inner or lower surface 13 of the membrane is coated with a thin film inert electrically conductive film material 14 which is also porous or permeable to the gas or vapor molecules to be sensed. This film 14 is of the desired inert sensing or working electrode material, such as platinum, gold or carbon. Thus the membrane 11 with its inert conductive film sensing electrode 14, preferably platinum, is a gas and vapor molecule permeable membrane. As mentioned above, the thickness of this electrode film 14 is exaggerated in the drawing for clarity. It will be observed that the sensing electrode film 14 extends from approximately the left edge of the membrane 11 to a line 15, near, but not at the right hand edge thereof. This film 14 is preferably sputtered onto the membrane. Next to the film 14 but spaced therefrom is another film 16 on membrane 13 which forms the reference electrode. The reference electrode film 16 is preferably of a metal/metal ion silver composition, $Ag/Ag^+$ or $Ag/AgCl$. The reference electrode film 16 is coated in a separate operation generally by a thin coating of conductive silver paste and drying at about 50° C. These two electrodes as shown are coplanar.

Beneath the membrane 11 with its two electrodes 14 and 16 is a thin layer electrolyte permeated region 17 in contact with the electrodes. The platinum (or other chosen inert material) film used for the sensing electrode does not dissolve in the electrolyte solution and does not interact with the solution. Beneath the electrolyte permeated region 17 is a nonconductive substrate 20, such as glass or ceramic, which rests against the case 21 or which has a reservoir space beneath it. At the right and left ends of the electrode assembly are a pair of counter electrodes 22 and 23, respectively. The counter electrodes, like the sensing electrodes, are of an inert conductive material such as platinum, gold or carbon. Electrical contact from the three electrodes to an external indication or alarm circuit may be provided at plug-in contacts 25. As is seen from the drawing, these counter electrodes lie in a different plane than the sensing and reference electrodes. An electrolyte reservoir surrounds the counter electrodes and may extend between the substrate 20 and the case 21 if desired. This particular cell configuration is highly sensitive and has a rapid response to the appearance of toxic gases or vapors.

The nonaqueous aprotic organic based solvent solution used in the cell has a high boiling point, low freezing point (that is, a wide operating temperature range between boiling point and freezing point) and low vapor pressure, and the loss of electrolyte will be very slow. If the preferred solvent γ-butyrolactone is selected, the boiling point is 202° C. and the freezing point is −43°. If the solvent propylene carbonate is selected, the boiling point is 241° C. and the freezing point is −49°. The solvent may also be N,N' dimethyl formamide. With any of these nonaqueous solvents the electrolyte added is lithium perchlorate, tetraalkylammonium perchlorate or tetraethylammonium perchlorate. Other aprotic organic solvents may also be used. The solvent readily absorbs and retains the toxic organic molecules because of their affinity and solubility in the solvent.

Figure 3:
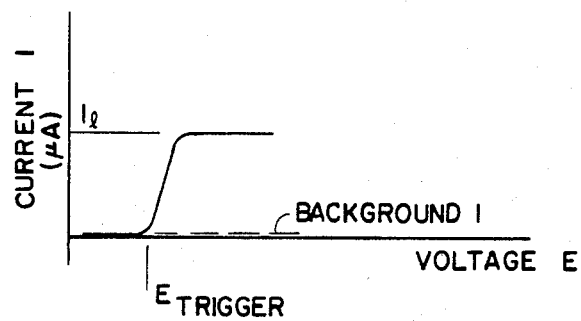
FIG. 3 is a graphical voltage-current curve.

In operation, a known potential to reduce or oxidize the compound of interest is applied to the sensing electrode vs. the reference electrode, and the current flow in the counter electrode or sensing electrode circuit is measured. This is shown graphically in FIG. 3, in which the current potential curve of the cell is shown. The amplitude of the current is a function of the concentration of chemical agents and the voltage $E_{trigger}$ is specific to the type of gas or vapor molecule being sensed. The current-potential curve of a thin-layer electrochemical cell can be described by diffusion-limiting current $I^l = (NFDAC_b/L)$ where N=the number of electrons involved in the redox reaction, F=Faraday constant, D=diffusion coefficient of the electroactive species, A=electrode area, C=bulk concentration of the species and L=electrolyte solution layer thickness (in the range 1 mm to 0.01 mm).

The cell configuration described herein is an experimental model and method for the detection of minute traces (1 ppb to 0.1 ppb) of toxic gases or vapors in a very short time interval (~2 seconds).

The embodiments of the invention in which an exclusive property or right is claimed are defined as follows:

1. A nonaqueous electrochemical cell sensor structure for detection of toxic gas or vapor molecules in the surrounding atmosphere comprising:
    an enclosure for electrochemical cell means, said enclosure having an opening on one face for admitting gases and vapors to be sensed from the surrounding atmosphere;
    a porous polymer membrane having an outer and an inner surface, a substantial portion of the inner surface of said membrane being coated with an inert thin conducting film which forms a sensing electrode, the outer surface at said opening being in communication with said atmosphere which may at times contain molecules of gas or vapor sought to be detected;
    a reference electrode fabricated on a separate portion of said inner surface by coating said membrane separate portion with a metal/metal ion film;
    a counter electrode inert film located beyond the edge of said membrane and electrically separated from said sensing and reference electrodes; and,
    a thin layer of nonaqueous electrolyte solution in said enclosure in contact with said electrodes.

2. The structure according to claim 1 in which said porous polymer membrane is polytetrafluoroethylene.

3. The structure according to claim 1 in which said film of inert conducting material is selected from the group consisting of platinum, gold and carbon.

4. The structure according to claim 1 in which said inert conducting material is platinum.

5. The structure according to claim 1 in which said metal/metal ion film is silver/silver ion.

6. The structure according to claim 1 in which said metal/metal ion film is silver/silver chloride.

7. The structure according to claim 1 in which the membrane is of a non-wetting material with respect to said nonaqueous electrolyte solution.

8. The structure according to claim 1 in which said reference electrode is planar with said sensing electrode.

9. The structure according to claim 1 in which said nonaqueous electrolyte solution consists of a solvent selected from the group consisting of γ-butyrolactone, propylene carbonate and N,N' dimethylformamide, and of an electrolyte selected from the group consisting of lithium perchlorate, tetraalkyl ammonium perchlorate and tetraethylammonium perchlorate.

10. A nonaqueous electrochemical cell sensor structure for detection of toxic gas or vapor molecules in the surrounding atmosphere comprising:
    a porous polymer membrane permeable to molecules of gas or vapor sought to be detected, said membrane having an outer surface in communication with said atmosphere which may at times contain molecules of said gas or vapor, said membrane having an inner surface of which a major portion is coated with a thin film of an inert conducting material which forms a permeable sensing electrode on said inner surface;
    a thin-film reference electrode planar with said sensing electrode fabricated on a remaining and separate portion of said inner surface near the edge of said membrane, by coating the separate portion with a metal/metal ion film to form the reference electrode;
    a counter electrode inert conducting material film located beyond the edge of said membrane and electrically separated from said sensing and reference electrodes; and,
    a thin layer of nonaqueous electrolyte solution in contact with said sensing, reference and counter electrodes.

11. The structure according to claim 10 in which said porous polymer membrane is polytetrafluoroethylene.

12. The structure according to claim 10 in which said film of inert conducting material is selected from the group consisting of platinum, gold and carbon.

13. The structure according to claim 10 in which said inert conducting material is platinum.

14. The structure according to claim 10 in which said metal/metal ion film is silver/silver ion.

15. The structure according to claim 10 in which said metal/metal ion film is silver/silver chloride.

16. The structure according to claim 10 in which the membrane is of a non-wetting material with respect to said nonaqueous electrolyte solution.

17. The structure according to claim 10 in which said reference electrode is planar with said sensing electrode.

18. The structure according to claim 10 in which said nonaqueous electrolyte solution consists of a solvent selected from the group consisting of γ-butyrolactone, propylene carbonate and N,N' dimethylformamide, and of an electrolyte selected from the group consisting of lithium perchlorate and tetraethylammonium perchlorate.

19. A nonaqueous electrochemical cell sensor structure for detection of trace quantities of gas or vapor molecules comprising:
    an electrochemical cell structure which includes a two-electrode supporting polymer membrane, said membrane being porous to molecules of gas or vapor sought to be detected;
    said porous membrane having an outer and an inner surface, the outer surface of which is in communication with an atmosphere which may contain molecules of said gas or vapor, the inner surface being coated in large measure by an inert thin conducting film forming a sensing electrode, and said inner surface being coated at a smaller separate area by a metal/metal ion film forming a reference electrode;
    said cell structure also including a counter electrode located beyond the edge of said membrane and in a plane different from said membrane and electrodes, said counter electrode comprising a film coating of conductive inert material; and, a thin layer of nonaqueous electrolyte solution adjacent and enveloping said sensing and reference electrode and also extending to envelop said counter electrode.

20. A nonaqueous electrochemical cell sensor structure for detection of toxic gas or vapor molecules in the surrounding atmosphere comprising:

an enclosure for electrochemical cell means, said enclosure having an opening on one face for admitting gases and vapors to be sensed from the surrounding atmosphere;

a porous polytetrafluoroethylene membrane having an outer and an inner surface, a substantial portion of the inner surface of said membrane being coated with an inert thin conducting film which forms a sensing electrode, the film material being selected from the group consisting of platinum, gold, and carbon, the outer surface at said opening being in communication with said atmosphere which may at times contain molecules of gas or vapor sought to be detected;

a reference electrode coated on a separate portion of said inner surface by coating said membrane separate portion with a silver/silver ion film, said silver/silver ion film being planar with said sensing electrode;

a counter electrode inert film located beyond the edge of said membrane and electrically separated from said sensing and reference electrodes; and, a thin layer of nonaqueous electrolyte solution in said enclosure in contact with said electrodes.

21. The structure according to claim 20 in which said nonaqueous electrolyte solution consists of a solvent selected from the group consisting of γ-butyrolactone, propylene carbonate and N,N' dimethylformamide, and of an electrolyte selected from the group consisting of lithium perchlorate, tetraalkyl ammonium perchlorate and tetraethylammonium perchlorate.

22. The structure according to claim 20 wherein said silver/silver ion is silver/silver chloride.

* * * * *